(12) United States Patent
Yanagi (10) Patent No.: US 10,280,083 B2
(45) Date of Patent: May 7, 2019

(54) METHOD FOR PRODUCING COMPLEXED PARTICLES

(71) Applicant: TOYOTA JIDOSHA KABUSHIKI KAISHA, Toyota-shi, Aichi-ken (JP)

(72) Inventor: Takuo Yanagi, Toyota (JP)

(73) Assignee: TOYOTA JIDOSHA KABUSHIKI KAISHA, Toyota-shi, Aichi-ken (JP)

( * ) Notice: Subject to any disclaimer, the term of this patent is extended or adjusted under 35 U.S.C. 154(b) by 0 days.

(21) Appl. No.: 15/822,723

(22) Filed: Nov. 27, 2017

(65) Prior Publication Data

US 2018/0148333 A1 May 31, 2018

(30) Foreign Application Priority Data

| Nov. 28, 2016 | (JP) | ................................. 2016-230655 |
| Mar. 23, 2017 | (JP) | ................................. 2017-057681 |
| Nov. 16, 2017 | (JP) | ................................. 2017-220711 |

(51) Int. Cl.

| *B01D 11/02* | (2006.01) |
| *C01B 17/40* | (2006.01) |
| *C01D 15/04* | (2006.01) |
| *B01D 9/00* | (2006.01) |
| *B01D 12/00* | (2006.01) |

(52) U.S. Cl.
CPC ............ *C01B 17/40* (2013.01); *B01D 9/0031* (2013.01); *B01D 11/0292* (2013.01); *C01D 15/04* (2013.01); *B01D 9/0054* (2013.01); *B01D 12/00* (2013.01); *B01D 2257/30* (2013.01); *G01N 2223/056* (2013.01)

(58) Field of Classification Search
CPC ....................... B01D 11/0292; B01D 2257/30; B01D 11/02; B01D 11/04; B01D 11/0492; B01D 2257/204; C01D 15/04; C01B 17/40; C01B 17/22
See application file for complete search history.

(56) References Cited

U.S. PATENT DOCUMENTS 6,017,500 A * 1/2000 Mehta ..................... C01B 17/66
423/179.5

FOREIGN PATENT DOCUMENTS

| JP | 07-316087 A | 12/1995 |
| JP | 2017-018872 A | 1/2017 |

* cited by examiner

*Primary Examiner* — Timothy C Vanoy
(74) *Attorney, Agent, or Firm* — Sughrue Mion, PLLC (57) ABSTRACT

A method for producing complexed particles including obtaining a good solvent solution, by dissolving $Li_2S$, and LiX (X is at least one selected from a group consisting of F, Cl, Br, and I) in a good solvent, and precipitating particles by contacting the good solvent solution with a poor solvent having a temperature at least 165° C. higher than the boiling point of the good solvent, to evaporate off the good solvent. The method further satisfies at least one of the following: (i) the good solvent solution being obtained by further dissolving $H_2S$ in the good solvent, and (ii) $H_2S$ being dissolved in the poor solvent.

12 Claims, 9 Drawing Sheets

METHOD FOR PRODUCING COMPLEXED PARTICLES

TECHNICAL FIELD

The present invention relates to a method for producing complexed particles.

BACKGROUND ART

Conventional techniques for precipitating particles from solution include methods in which a solution is heated in a container to evaporate off and remove the solvent and obtain particles (hereunder referred to a s "dry evaporation methods"), methods in which a solution is sprayed into hot air to evaporate the solvent in a gas phase, and precipitate particles as a dry powder (hereunder referred to as "spray dry methods"), and methods in which a solution of a solute dissolved in a good solvent is added dropwise to a heated poor solvent and the good solvent is evaporated off, to obtain a slurry of the particles and the poor solvent (hereunder referred to as "common methods using good solvent and poor solvent").

A specific example of common methods using good solvent and poor solvent is described in Patent Document 1. Patent Document 1 discloses a method consisting of dropping a good solvent into a poor solvent heated to a temperature higher than the good solvent, wherein the difference between the boiling point of the good solvent and the heating temperature of the poor solvent is about 40° C.

PRIOR ART DOCUMENTS

Patent Documents

[Patent Document 1] Japanese Unexamined Patent Publication No. H7-316087

DISCLOSURE OF THE INVENTION

Problems to be Solved by the Invention

Dry evaporation methods, spray dry methods and common methods using good solvent and poor solvent are all employed as methods for precipitating particles. In such methods, the rate of solvent evaporation is relatively slow. Therefore, the particles precipitate slowly by crystal growth, and it is difficult to obtain particles with low crystal growth. In addition, when particles are precipitated from a solution in which a plurality of raw material components have been dissolved, since each raw material component precipitates by crystallizing separately in order starting with the component having the lowest solubility, it is difficult to obtain particles in which a plurality of raw material components are in a complexed state.

The aforementioned methods are therefore poorly efficient when the goal is to produce particles comprising different raw material components in a complexed state.

It is thus an object of the present invention to provide a method for efficiently producing particles with a plurality of raw material components in a complexed state, and having low crystal growth.

"Complexed state" refers to a plurality of raw material components being highly and uniformly dispersed in particles and mixed in a state in which there is low growth of the crystal phase of each individual raw material component in the particles. Low growth of the crystal phase of each individual raw material component in the particles can be confirmed by, for example, analyzing the shifts of crystal peaks by XRD analysis.

Means for Solving the Problems

The inventor of the present invention has found that the object of the present invention can be achieved by the means described below.

[Embodiment 1] A method for producing complexed particles,
wherein the method comprises:
obtaining a good solvent solution, by dissolving $Li_2S$, and LiX (X is at least one selected from a group consisting of F, Cl, Br, and I) in a good solvent, and
precipitating particles by contacting the good solvent solution with a poor solvent having a temperature at least 165° C. higher than the boiling point of the good solvent, to evaporate off the good solvent; and,
wherein the method satisfies at least one of the following:
(i) the good solvent solution being obtained by further dissolving $H_2S$ in the good solvent, and (ii) $H_2S$ being dissolved in the poor solvent.

[Embodiment 2] The method according to embodiment 1, wherein the LiX is LiI and LiBr.

[Embodiment 3] The method according to embodiment 1 or 2, wherein at least the (i) is satisfied.

[Embodiment 4] The method according to embodiment 3, wherein in the (i), the good solvent solution is obtained by further dissolving $H_2S$ in the good solvent by blowing $H_2S$ into the good solvent.

[Embodiment 5] The method according to any of embodiments 1 to 4, wherein at least the (ii) is satisfied.

[Embodiment 6] The method according to embodiment 5, wherein in the (ii), the $H_2S$ is dissolved in the poor solvent by blowing $H_2S$ into the poor solvent.

[Embodiment 7] The method according to any of embodiments 1 to 6, wherein the ratio of the LiX (X is at least one selected from a group consisting of F, Cl, Br, and I) is 0.30 mol to 0.60 mol based on 1 mol of $Li_2S$.

[Embodiment 8] A method for producing complexed particles,
wherein the method comprises:
obtaining a good solvent solution, by dissolving LiHS, and LiX (X is at least one selected from a group consisting of F, Cl, Br, and I) in a good solvent, and
precipitating particles by contacting the good solvent solution with a poor solvent having a temperature at least 165° C. higher than the boiling point of the good solvent to evaporate off the good solvent.

[Embodiment 9] The method according to embodiment 8, wherein the ratio of the LiX (X is at least one selected from a group consisting of F, Cl, Br, and I) is 0.30 mol to 0.60 mol based on 1 mol of LiS.

[Embodiment 10] The method according to embodiment 8 or 9, wherein the LiX is LiI and LiBr.

[Embodiment 11] The method according to any of embodiments 1 to 10, wherein the contacting the good solvent solution with the poor solvent is by dropping, spraying, or injecting the good solvent solution into the poor solvent.

[Embodiment 12] The method according to embodiment 11, wherein the contacting the good solvent solution with the poor solvent is by dropping the good solvent solution into the poor solvent.

Effects of the Invention

According to the present invention, particles in which a plurality of raw material components, specifically $Li_2S$ and LiX (X is at least one selected from a group consisting of F, Cl, Br, and I), are in a complexed state, and in which there is low crystal growth, can be efficiently produced.

BEST MODE FOR CARRYING OUT THE INVENTION

Embodiments of the present invention will now be explained in detail. The present invention is not limited to the embodiments described below, and various modifications may be implemented within the scope of the gist thereof.

The first aspect the present invention relates to, a method for producing complexed particles, wherein the method comprises:

obtaining a good solvent solution, by dissolving $Li_2S$, and LiX (X is at least one selected from a group consisting of F, Cl, Br, and I) in a good solvent, and precipitating particles by contacting the good solvent solution with a poor solvent having a temperature at least 165° C. higher than the boiling point of the good solvent, to evaporate off the good solvent; and, wherein the method satisfies at least one of the following:

(i) the good solvent solution being obtained by further dissolving $H_2S$ in the good solvent, and (ii) $H_2S$ being dissolved in the poor solvent.

The second aspect the present invention relates to, a method for producing complexed particles, wherein the method comprises:

obtaining a good solvent solution, by dissolving LiHS, and LiX (X is at least one selected from a group consisting of F, Cl, Br, and I) in a good solvent, and precipitating particles by contacting the good solvent solution with a poor solvent having a temperature at least 165° C. higher than the boiling point of the good solvent to evaporate off the good solvent.

While it is not our intention to be restricted to any particular principle, it is believed that the principle of action according to the present invention is as follows.

Conventionally, complexed particles cannot be recovered efficiently for the following reasons in the case of using the dry evaporation method, spray dry method or common methods using good solvent and poor solvent.

In the case of the dry evaporation method, large particles that have undergone slow crystal growth end up precipitating. Consequently, in the case of the dry evaporation method, it is difficult to obtain particles in which a plurality of raw material components is in a complexed state.

In the case of the spray dry method, although a good solvent can be evaporated faster than in the case of the dry evaporation method, the rate at which the good solvent evaporates is not sufficiently fast. Consequently, a plurality of raw material components tends to precipitate separately according to their respective solubility. Since time is required to dry the particles, particles in the gaseous phase tend to mutually collide and aggregate with other particles during the course of drying. Precipitated particles also end up aggregating on the bottom of a container in the case they are not adequately dried. Consequently, it is difficult to obtain particles in which a plurality of raw material components is in a complexed state when using the spray dry method.

In the case of using the common methods using good solvent and poor solvent, when a good solvent solution is contacted with a poor solvent having a low temperature difference with the boiling point of the good solvent, the good solvent solution initially mixes with the poor solvent resulting in a mixed solution. Subsequently, the good solvent gradually evaporates due to the heat of the poor solvent and leaves this mixed solution. In this case, since the rate at which the good solvent leaves the mixed solution is slow, raw material components precipitate in the form of large particles that have undergone crystal growth. Since the raw material components each precipitate slowly in order starting with the component having the lowest solubility, they end up precipitating as mutually separate particles and have difficulty in precipitating in the form of a complex. Consequently, it is difficult to obtain particles in which a plurality of raw material components is in a complexed state in the case of the common methods using good solvent and poor solvent.

In contrast, in the case the solvent evaporation rate during particle precipitation is sufficiently fast, a plurality of raw material components is in a complexed state without being separated according to their respective solubility, and precipitates in the form of a plurality of complexed particles without undergoing crystal growth.

In the present invention, when a good solvent solution in which raw material components (for example, $Li_2S$ and LiX (X is at least one selected from a group consisting of F, Cl, Br, and I)) are dissolved, is contacted with a poor solvent having a large temperature difference therewith of at least 165° C. higher than the boiling point of the good solvent, the good solvent is able to be instantaneously evaporated off at the interface between the good solvent solution and the poor solvent. Consequently, the raw material components precipitate in the form of particles in which the raw material components are in a complexed state without being separated according to their respective solubility and without undergoing crystal growth.

Furthermore, the present invention is a method for precipitating particles by contacting a good solvent solution, obtained by dissolving raw material components in a good solvent, with a poor solvent having a temperature at least 165° C. higher than the boiling point of the good solvent to evaporate off the good solvent and precipitate particles; wherein, Li$_2$S and LiX (X is at least one selected from a group consisting of F, Cl, Br, and I) are used for the raw material components, and at least one of the following is satisfied: (i) the good solvent solution being obtained by further dissolving H$_2$S in addition to these raw material components, and (ii) H$_2$S being dissolved in the poor solvent. Under such conditions, H$_2$S is dissolved in at least one of the good solvent and the poor solvent. Li$_2$S forms LiHS in the presence of H$_2$S as a result of S$^{2-}$ ions being converted to SH$^-$ ions by the reaction indicated below.

$$Li_2S + H_2S \rightleftharpoons 2LiHS \quad \text{[Chemical 1]}$$

LiHS easily changes to Li$_2$S by releasing H$_2$S. When particles precipitate, the good solvent is torn away due to vibration of the crystal matrix that occurs when H$_2$S is released. Consequently, it is difficult for the good solvent to be incorporated in the precipitated particles. In addition, in the case of using a good solvent having a relatively low affinity with LiHS (for example, methanol), the good solvent is easily eliminated. Consequently, it is difficult for the good solvent to be incorporated in the precipitated particles. Furthermore, in the case of using a good solvent having a relatively low reactivity with LiSH, it is difficult for new stable crystals of the good solvent with Li, S, and the like, to form.

It is therefore thought to be able to reduce the amount of good solvent remaining in the produced particles by dissolving H$_2$S in at least one of the good solvent and poor solvent and converting Li$_2$S in the good solvent solution to LiHS.

As a result of reducing the amount of good solvent remaining in the particles, it is not necessary to heat to a temperature equal to or higher than the phase transition temperature in order to remove the good solvent incorporated in the particles, and unnecessary changes in the shape or complexed state of the particles can be inhibited. In the case of using the produced particles as raw material particles of the solid electrolyte of a lithium battery, for example, reducing the amount of good solvent remaining in the particles makes it possible to inhibit decreases in lithium ion conductivity attributable to the presence of good solvent.

The aforementioned effect is thought to be demonstrated due to the conversion of Li$_2$S of the raw material components to LiHS by H$_2$S. In the present invention, similar effects are demonstrated even if LiHS is used instead of Li$_2$S as a raw material component. This embodiment is as described below.

A method for producing complexed particles,
wherein the method comprises:
obtaining a good solvent solution, by dissolving LiHS, and LiX (X is at least one selected from a group consisting of F, Cl, Br, and I) in a good solvent, and
precipitating particles by contacting the good solvent solution with a poor solvent having a temperature at least 165° C. higher than the boiling point of the good solvent to evaporate off the good solvent.

(Good Solvent)

In the present invention, a good solvent refers to a solvent that is able to completely or partially dissolve the raw material components of the present invention and has higher solubility with respect to the raw material components than that of the poor solvent used in the present invention. There are no particular limitations on the good solvent of the present invention and examples thereof include methanol, water and toluene. In addition, from the viewpoint of affinity and reactivity with LiHS, solvent having polar group (OH group), for example methanol, is preferred. For example, in the case of using methanol as a good solvent, the methanol is easily eliminated since LiHS has low affinity with the polar group (OH group) that composes the methanol. Consequently, it is difficult for methanol to be incorporated in the precipitated particles. Moreover, since the level of reactivity between methanol and LiHS is low, it is difficult for new stable crystals of methanol and Li, S, and the like, to form.

(Raw Material Components)

In the present invention, raw material components refer to components serving as raw materials of particles (also referred to as "complexed particles") produced according to the present invention, and include Li$_2$S or LiHS, and LiX (X is at least one selected from a group consisting of F, Cl, Br, and I). For LiX (Lithium halide), X is at least one selected from a group consisting of F, Cl, Br, and I. Also, Li$_2$S or LiHS, and LiX (X is at least two selected from a group consisting of F, Cl, Br, and I) may be used as the raw materials. For example, Li$_2$S, LiI, and LiBr may be used as the raw materials. Similarly, LiHS, LiI, and LiBr may also be used as the raw materials.

The ratio of each component in the raw material components is such that the ratio of LiX (X is at least one selected from a group consisting of F, Cl, Br, and I) may be each 0.30 mol to 0.60 mol based on 1 mol of Li$_2$S or LiHS. The ratio of LiX (X is at least one selected from a group consisting of F, Cl, Br, and I) based on 1 mol of Li$_2$S or LiHS may be 0.30 mol or more, 0.32 mol or more, 0.35 mol or more, 0.60 mol or less, 0.57 mol or less, or 0.55 mol or less. It should be noted that when use plural kinds of LiX (X is at least one selected from a group consisting of F, Cl, Br, and I) in the same time, the total ratios of the plural kinds of LiX (X is at least one selected from a group consisting of F, Cl, Br, and I) in the same time may be within the above ranges, based on 1 mol of Li$_2$S or LiHS. Therefore, for example, when LiX and LiBr are used as LiX at the same time, the total ratios of LiX and LiBr may be within the above ranges.

There are no particular limitations on the method used to dissolve the raw material components in a good solvent. For example, LiHS or Li$_2$S, and LiX (X is at least one selected from a group consisting of F, Cl, Br, and I) may be dissolved in a good solvent in the form of particles (solid form) at their respective prescribed ratios. It may be described whit a specific example. For example, when LiX and LiBr are used as LiX at the same time, the following methods may be mentioned, but no limited. LiHS, LiI and LiBr may also be dissolved in a good solvent at their respective prescribed ratios, similarly Li$_2$S, LiI and LiBr may also be dissolved in a good solvent at their respective prescribed ratios. When the good solvent solution is obtained by further dissolving H$_2$S in the good solvent, prior to or after dissolving Li$_2$S, LiI and LiBr in a good solvent at their respective prescribed ratios, H$_2$S gas may be dissolved by blowing in, for example, to transform the S$^{2-}$ ions of Li$_2$S to SH− ions, convert to LiHS and obtain a good solvent solution in which LiHS, LiI and LiBr are dissolved. A description of the dissolution of H$_2$S in this case will be subsequently described.

(Good Solvent Solution)

The good solvent solution used in the present invention is a solution obtained by dissolving raw material components in a good solvent. Although there are no particular limitations thereon, the total concentration of a plurality of raw material components in the good solvent solution is preferably 5 g/l or more, 10 g/l or more, 20 g/l or more or 50 g/l or more. This is because, a higher concentration of raw material components dissolved in the good solvent solution will allow the raw material components to be recovered in a more complexed state, that is, a higher concentration of raw material components in the good solvent solution allows more complexed particles to be obtained. This is because a higher concentration of dissolved raw material components further increases the viscosity of the solution, resulting in inhibition of movement of the ions in the solution, and when the good solvent has been evaporated, the raw material components tend to precipitate by crystallization without changing their arrangement in the solution.

(Poor Solvent)

The poor solvent used in the present invention is a solvent for which the solubility of raw material components therein is lower than that of the good solvent. The solubility of the resulting particles in the poor solvent used in the present invention may be also low. The poor solvent of the present invention is heated to a temperature at least 165° C. higher than the boiling point of the good solvent. The difference between the temperature at which the poor solvent is heated and the boiling point of the good solvent may be 165° C., and also may be 170° C. or more, 175° C. or more, 180° C. or more or 190° C. or more. There are no particular limitations on the heating method used to set to a temperature at least 165° C. higher than the boiling point of the poor solvent. Any method can be used for the heating method provided it allows the poor solvent to be heated to the target temperature. The evaporation rate of the good solvent increases the higher the temperature of the poor solvent is relative to the boiling point of the good solvent. On the basis thereof, although there is no upper limit on the heating temperature of the poor solvent, it is preferably equal to or below the boiling point of the poor solvent.

Although there are no particular limitations thereon, the poor solvent used in the present invention is that which is heated to a temperature at least 165° C. higher than the boiling point of the good solvent. Consequently, a poor solvent is used that has a boiling point that is high enough to enable it to be heated to that temperature at normal pressure. The poor solvent is a solvent that has a comparatively high boiling point, and examples thereof include dodecane (boiling point: about 216° C.) and tridecane (boiling point: about 235° C.) The poor solvent is preferably selected in consideration of the relationship thereof with the boiling point of the good solvent used in the present invention. More specifically, a poor solvent is preferably selected that has a boiling point at least 165° C. higher than the boiling point of the good solvent. For example, tridecane (boiling point: about 235° C.) can be selected for the poor solvent in the case of using methanol (boiling point: about 65° C.) for the good solvent.

(Dissolution of $H_2S$)

When the method for producing complexed particles in the present invention uses $Li_2S$ as a raw material component, at least one of the following conditions is satisfied: the good solvent solution being obtained by further dissolving $H_2S$ in the good solvent, and $H_2S$ being dissolved in the poor solvent. That is, the method for producing complexed particles in the present invention satisfies at least one of (i) and (ii) mentioned above. The method for producing complexed particles in the present invention may satisfy at least (i), or satisfy at least (ii), or may satisfy (i) and (ii) at the same time. The concentration of $H_2S$ in at least one of the good solvent and poor solvent following the dissolution thereof is arbitrary. The concentration of $H_2S$ in these solvents is, for example, the saturated concentration.

A method consisting of blowing $H_2S$ into these solvents, such as by introducing $H_2S$ by bubbling, may be employed to dissolve the $H_2S$ in the good solvent and/or poor solvent. At this time, $H_2S$ may be blown in alone or a mixed gas of $H_2S$ and an inert gas may be blown in. Examples of inert gas include nitrogen, helium and argon. During bubbling, the supplied and discharged amounts of $H_2S$ may be monitored, and the concentration of $H_2S$ in these solvents may be evaluated to have reached the saturated concentration when the amounts of both solvents are roughly equal and have stabilized.

As was previously described, the expected effect of the present invention is thought to be demonstrated as a result of $Li_2S$ of the raw material components being converted to LiHS due to the presence of $H_2S$. Similar effects are therefore obtained regardless of whether the $H_2S$ is dissolved in the good solvent or poor solvent. However, in the case the solubility of $H_2S$ in the poor solvent is low, for example when the poor solvent is tridecane, $H_2S$ is preferably at least dissolved in the good solvent from the viewpoint of allowing the reaction between $Li_2S$ and $H_2S$ to proceed adequately.

(Contact Method)

In the present invention, the good solvent solution contacts the poor solvent that has been heated to a temperature at least 165° C. higher than the boiling point of the good solvent. There are no particular limitations on the method used to contact the good solvent solution with the poor solvent. Specific examples thereof include a method consisting of dropping the good solvent solution from above the liquid surface of the poor solvent, a method consisting of spraying the good solvent solution from above the liquid surface of the poor solvent, and method consisting of injecting liquid droplets of the good solvent solution from the end of a nozzle immersed in the poor solvent. The nozzle used when contacting the good solvent solution with the poor solvent may be, for example, a tubular nozzle, porous body nozzle or spray nozzle. Specific examples of spray nozzles include a pressure nozzle, injector, single fluid spray nozzle and two-fluid spray nozzle.

Although there are no particular limitations on the diameter of droplets of the good solvent solution when contacting the good solvent solution with the poor solvent, from the viewpoint of facilitating instantaneous evaporation, the diameter of the droplets is preferably 1 mm or less, more preferably 500 µm or less and even more preferably 100 µm or less. From the viewpoint of efficiently obtaining complexed particles, the diameter of the droplets is preferably 1 µm or more, more preferably 5 µm or more and even more preferably 10 µm or more.

In the present invention, the poor solvent is heated to a temperature that is significantly higher than the good solvent solution. Consequently, the good solvent present in the good solvent solution evaporates off the instant the good solvent solution contacts the poor solvent, and particles precipitate in which raw material components are highly complexed in the vicinity of the interface with the poor solvent.

Figure 1A:
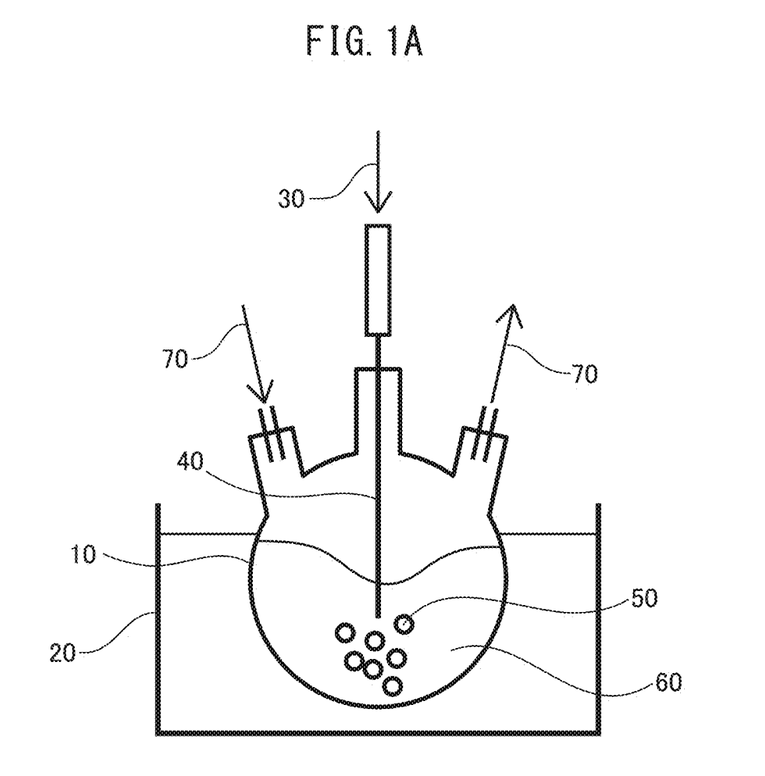
FIG. 1A illustrates an example of an embodiment of the method of the present invention.
Figure 1B:
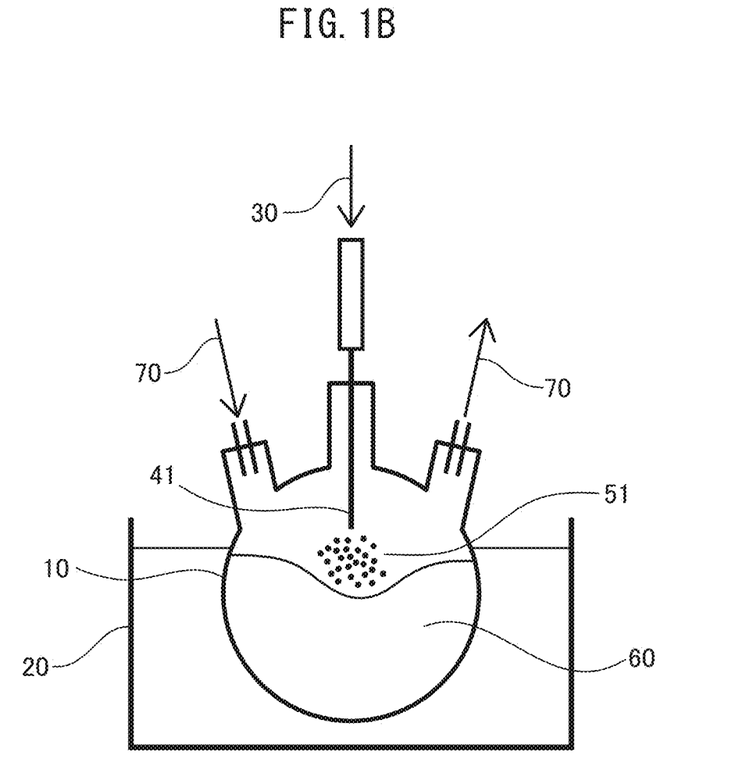
FIG. 1B illustrates another example of an embodiment of the method of the present invention.

The method of the present invention can be carried out with the devices illustrated in FIGS. 1A and 1B, for example. FIG. 1A illustrates an example of spraying the good solvent solution from above the liquid surface of the poor solvent, while FIG. 1B illustrates an example of injecting the good solvent solution into the poor solvent.

In the method indicated in FIG. 1A, a poor solvent (60) is first placed in a reaction vessel (10) followed by heating the poor solvent (60) to a temperature at least 165° C. higher than the boiling point of a good solvent with a heating device (20). Subsequently, a good solvent solution (30) is contacted with the high-temperature poor solvent (60) by injecting therein in the form of micro droplets of good solvent solution (50) with, for example, a single-fluid spraying nozzle (40). The good solvent present in droplets of good solvent solution (50) evaporates off the instant the injected droplets of good solvent solution (50) contact the high-temperature poor solvent (60), and particles in which raw material components are complexed precipitates in the poor solvent (60). The evaporated good solvent is discharged outside the reaction vessel (10) together with flowing gas (70) that has been passed through the vessel in advance.

The method indicated in FIG. 1B may be carried out in roughly the same manner as the method indicated in FIG. 1A with the exception of contacting the good solvent solution (30) by spraying onto the liquid surface of the heated poor solvent (60) in the form of an atomized good solvent solution (51) with, for example, a spray nozzle (41). Good solvent present in the atomized good solvent solution (51) evaporates off the instant the sprayed atomized good solvent solution (51) contacts the liquid surface of the heated poor solvent (60), and particles in which raw material components are complexed precipitate in the poor solvent (60). The evaporated good solvent is discharged outside the vessel together with the flowing gas (70) that has been passed through the vessel in advance.

Figure 1C:
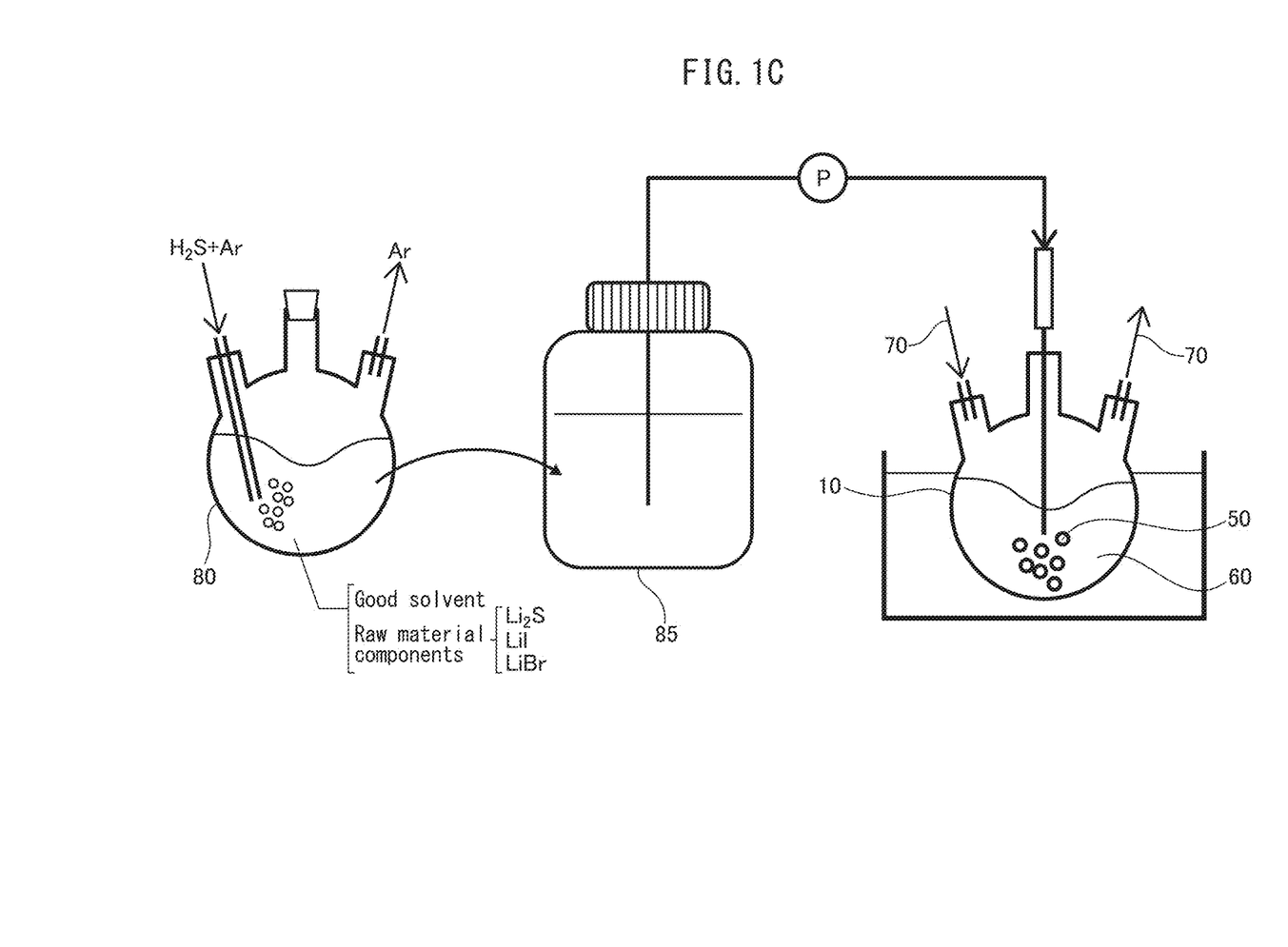
FIG. 1C illustrates an example of a method for carrying out the method of the present invention by dissolving $H_2S$ in a good solvent.

FIG. 1C illustrates an example of the method of the present invention. The method indicated in FIG. 1C is an example of the case in which $H_2S$ is dissolved in a good solvent.

According to the method indicated in FIG. 1C, after having dissolved raw material components such as $Li_2S$, LiI and LiBr in a good solvent in a suitable vessel (80), for example, to obtain a good solvent solution, $H_2S$ is blown into the resulting good solvent solution to dissolve the $H_2S$ in the good solvent. $Li_2S$ present in the good solvent solution is converted to LiHS due to the presence of the dissolved $H_2S$. $H_2S$ may also be dissolved in the good solvent prior to dissolving the $Li_2S$, LiI and LiBr.

Blowing in of the $H_2S$ is carried out by means of a tube inserted into the good solvent or good solvent solution, for example. $H_2S$ may be blown in as a mixed gas with a suitable inert gas such as Ar. In this case, although substantially only Ar is discharged from the vessel (80) during initial blowing, as the concentration of $H_2S$ in the solution approaches saturation, $H_2S$ is discharged along with Ar. The concentration of $H_2S$ in the solution can be estimated by monitoring the composition of this discharged gas.

Next, the good solvent solution in which the concentration of $H_2S$ has become sufficiently high is transferred to a reaction raw material vessel (85) and droplets of the good solvent solution (50) are injected into the poor solvent (60) present in the reaction vessel (10) using a pump (P), for example. At this time, flowing gas (70) may be passed through the reaction vessel (10).

Figure 1D:
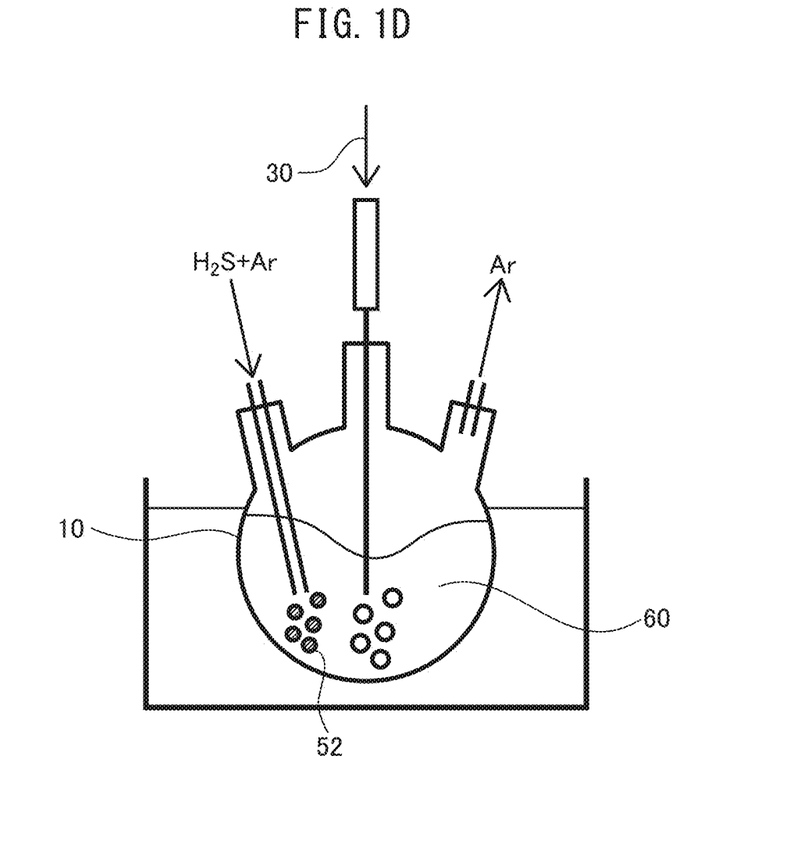
FIG. 1D illustrates an example of a method for carrying out the method of the present invention by dissolving $H_2S$ in a poor solvent.

FIG. 1D illustrates an example of method for carrying out the method of the present invention by dissolving $H_2S$ in a poor solvent.

According to the method illustrated in FIG. 1D, $H_2S$ can be dissolved in the poor solvent (60) by blowing $H_2S$ into the poor solvent (60) instead of allowing flowing gas (70) to pass through the reaction vessel (10) as in the method indicated in FIG. 1A. Blowing in of the $H_2S$ is carried out, for example, by means of a tube inserted into the poor solvent. $H_2S$ may be blown in as a mixed gas with a suitable inert gas such as Ar. In this case, the concentration of $H_2S$ in the poor solvent can be estimated by monitoring the composition of the discharged gas in the same manner as in the case of FIG. 1C. In the case of using the method shown in FIG. 1D, contact between the good solvent solution and poor solution is preferably initiated after the concentration of $H_2S$ in the poor solvent has become sufficiently high.

In the method of the present invention, the aspect shown in FIG. 1C and the aspect shown in FIG. 1D may carried out redundantly, and may be carried out by dissolving $H_2S$ in both the good solvent and poor solvent.

FIGS. 1C and 1D indicate a method in which the good solvent solution and poor solvent are contacted by injecting micro droplets of the good solvent solution (50) into the poor solvent (60). However, other contact methods may also be employed in the methods of FIGS. 1C and 1D.

The aforementioned FIGS. 1A to 1D are not intended to limit embodiments of the present invention to the aspects shown.

EXAMPLES

Example 1

8.33 g of $Li_2S$, 4.04 g of LiI and 2.63 g of LiBr as raw material components were dissolved in 300 mL of methanol as a good solvent. Trace amounts of insoluble components (such as $Li_2CO_3$) contained in each of the raw material components were removed by suction filtration using a 0.2 μm mesh filter to prepare a methanol solution in which $Li_2S$, LiI and LiBr (molar ratio: 6:1:1) were dissolved so that the total concentration of these raw material components in the methanol solution was 50 g/L. This methanol solution was placed in a 500 mL round bottom flask. A mixed gas of $H_2S$ and Ar (molar ratio: 1:1) was blown into the methanol solution in the flask for 1.5 hours at a flow rate of 400 mL/min using a bubbling tube (see FIG. 1A). As a result of carrying out this procedure, $S^{2-}$ ions of the $Li_2S$ were converted to $SH^-$ ions to prepare a good solvent solution in which LiHS, LiI and LiBr (molar ratio: 12:1:1) were dissolved.

350 mL of tridecane (boiling point: about 235° C.) as a poor solvent was placed in a 500 mL round bottom flask and then placed in an oil bath heated to 230° C. After the temperature of the poor solvent had stabilized, the good solvent solution was passed through a tubular nozzle (1/16-inch PFA tube, inner diameter: 500 μm) immersed in the poor solvent and injected into the poor solvent over the course of 20 minutes at about 8 mL/min. Subsequently, injection was discontinued and the temperature was held at 230° C. for 1 hour. The precipitate that precipitated in the poor solvent was collected by filtering inside a glove box to obtain particles of Example 1. The difference between the boiling point of the good solvent and the temperature of the poor solvent in Example 1 was about 165° C.

Reference Example 1

8.33 g of $Li_2S$, 4.04 g of LiI and 2.63 g of LiBr as raw material components were dissolved in 300 mL of methanol as a good solvent. Trace amounts of insoluble components (such as $Li_2CO_3$) contained in each of the raw material components were removed by suction filtration using a 0.2 μm mesh filter to prepare a methanol solution in which the $Li_2S$, LiI and LiBr (molar ratio: 6:1:1) were dissolved such that the total concentration of raw material components in the methanol was 50 g/L. This methanol solution was used for the good solvent solution in Reference Example 1.

Particles of Reference Example 1 were obtained in the same manner as Example 1 with the exception of spraying the good solvent solution of Reference Example 1 onto the poor solvent over the course of 5 minutes at about 50 ml/min using a pressure nozzle.

Comparative Example 1

Particles of Comparative Example 1 were obtained in the same manner as Example 1 with the exception of making the total concentration of $Li_2S$, LiI and LiBr as raw material components in the good solvent solution to be 50 g/L, making the temperature of tridecane as the poor solvent to be 80° C., continuously distilling off the good solvent while dropping the good solvent solution into the poor solvent while stirring at normal pressure for 10 minutes at a droplet diameter of about 2 mm and at a rate of 5 ml/min, and continuing to further distill off the good solvent by evaporating for about 30 minutes while holding the temperature of the round bottom flask at 80° C. after having finished dropping in the good solvent solution.

The difference between the boiling point of the good solvent and the heating temperature of the poor solvent in Comparative Example 1 was about 15° C.

Comparative Example 2

$Li_2S$, LiI and LiBr as raw material components were added to 1-pentanol (boiling point: about 138° C.) as a good solvent so that the total concentration of the raw material components in the good solvent solution was 20 g/L. Hydrogen sulfide was passed through the resulting liquid while stirring to convert the $Li_2S$ to LiHS, dissolve all of the raw material components, and prepare a good solvent solution. 400 mL of tridecane as a poor solvent were placed in a 1,000 mL round bottom flask and then placed in an oil bath heated to 230° C. After the temperature of the poor solvent had stabilized, the good solvent solution was injected into the poor solvent over the course of 11 minutes at about 50 mL/min by passing through a tubular nozzle immersed in the poor solvent. The vapor resulting from evaporation was liquefied and recovered by cooling with a condenser tube (at the temperature of tap water). The difference between the boiling point of the good solvent and the heating temperature of the poor solvent in Comparative Example 2 was about 92° C.

Since vapor continued to be generated even following completion of dropping, the temperature of the round bottom flask remained the same. After about 30 minutes had elapsed, there was hardly any recovered liquid coming out of the condenser tube. After another 30 minutes had elapsed, heating was discontinued after maintaining the temperature of the round bottom flask. The round bottom flask was placed in a glove box and the contents were filtered in an argon atmosphere to separate into a solid fraction and liquid fraction. The filtrate was removed from the glove box and when the smell thereof was examined, the smell was confirmed to be that of 1-pentanol as the good solvent.

Since vapor was continued to be generated even after completion of dropping and the smell of 1-pentanol as the good solvent was confirmed in the filtrate, the good solvent present in the good solvent solution dropped into the poor solvent was thought to have mixed with the poor solvent without instantaneously evaporating at the interface therewith, thereby resulting in a mixed solvent.

On the basis thereof, simply heating the poor solvent to a temperature roughly 92° C. (about 230° C.-about 138° C.) higher than the boiling point of the good solvent is thought to not permit instantaneous evaporation of the good solvent at the interface with the poor solvent even if the good solvent solution is contacted with the poor solvent.

(Evaluation 1)

Figure 2:
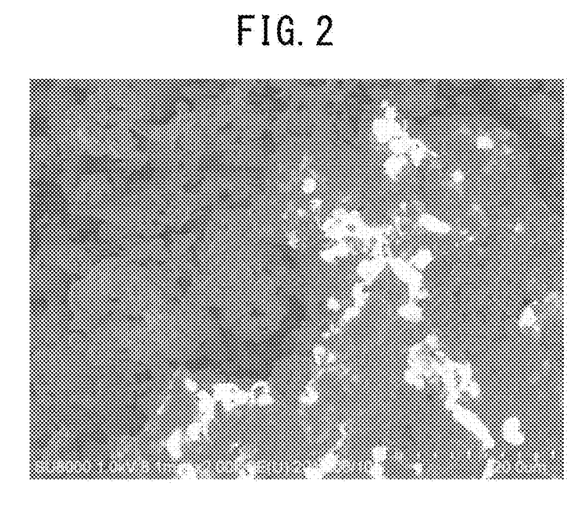
FIG. 2 is a scanning electron micrograph of particles obtained according to the method of Comparative Example 1.
Figure 3:
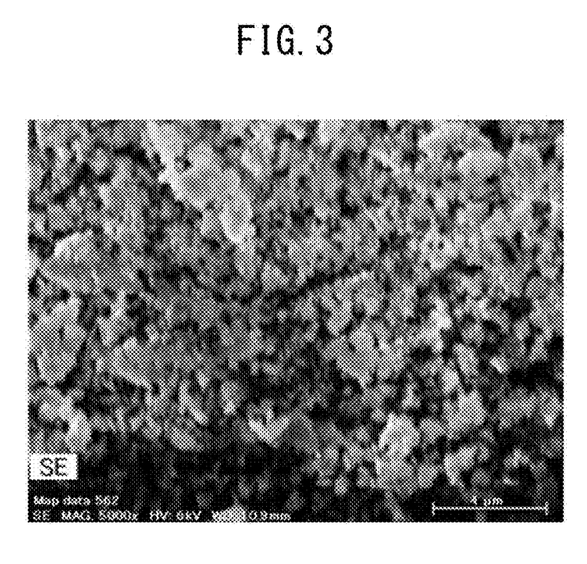
FIG. 3 is a scanning electron micrograph of particles obtained according to the method of Example 1.
Figure 4:
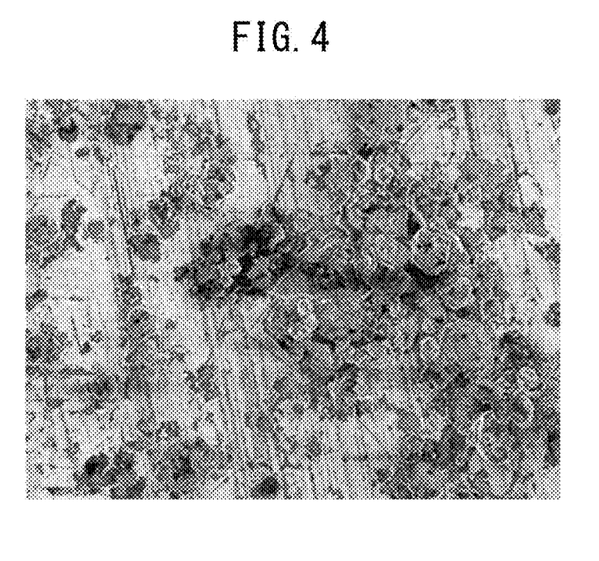
FIG. 4 is a scanning electron micrograph of particles obtained according to the method of Reference Example 1.

FIGS. 2, 3 and 4 indicate the results of observing precipitates obtained according to the precipitation methods of Comparative Example 1, Example 1 and Reference Example 1, respectively, using a scanning electron microscope.

Large particles having a particle diameter of about 50 μm or larger were observed in FIG. 2, which depicts a scanning electron micrograph of the precipitate of Comparative Example 1. Those areas in FIG. 2 of high brightness indicate areas where iodine and/or bromine are localized.

Particles cannot be obtained under the conditions of Comparative Example 1 since particles having a large particle diameter precipitated in FIG. 2. The precipitated particles can also not be in a complexed state since areas are observed where iodine and/or bromine are localized. These findings suggest that, since the good solvent evaporated slowly, the concentration of good solvent in the mixed solvent of the poor solvent and good solvent decreased slowly, which in addition to resulting in the occurrence of slow crystal growth, caused the raw material components to respectively precipitate in the form of different crystals due to differences in solubility.

Particles having a particle diameter of 0.1 μm to 2 μm were confirmed in FIG. 3, which is a scanning electron micrograph of the precipitate of Example 1.

It can be determined from FIG. 3 that, in the case of having carried out precipitation according to the method of the present invention, a precipitate was recovered in the form of particles having a particle diameter of 2 μm or less. This suggests that, as a result of injecting the good solvent solution into the poor solvent, the good solvent in the good solvent solution evaporated off instantaneously when contacted with the poor solvent, thereby resulting in instantaneous precipitation of the raw material components dissolved in the good solvent solution.

Particles having a particle diameter of 0.1 μm to 2 μm were confirmed in FIG. 4, which is a scanning electron micrograph of the precipitate of Reference Example 1.

It can be determined from FIG. 4 that, in the case of having carried out precipitation according to the method of Reference Example 1, a precipitate was recovered in the form of particles having a particle diameter of 2 μm or less. This suggests that the good solvent in the good solvent solution instantaneously evaporated off on the liquid surface of the poor solvent as a result of spraying, thereby resulting in instantaneous precipitation of the raw material components dissolved in the good solvent solution.

(Evaluation 2)

Figure 5:
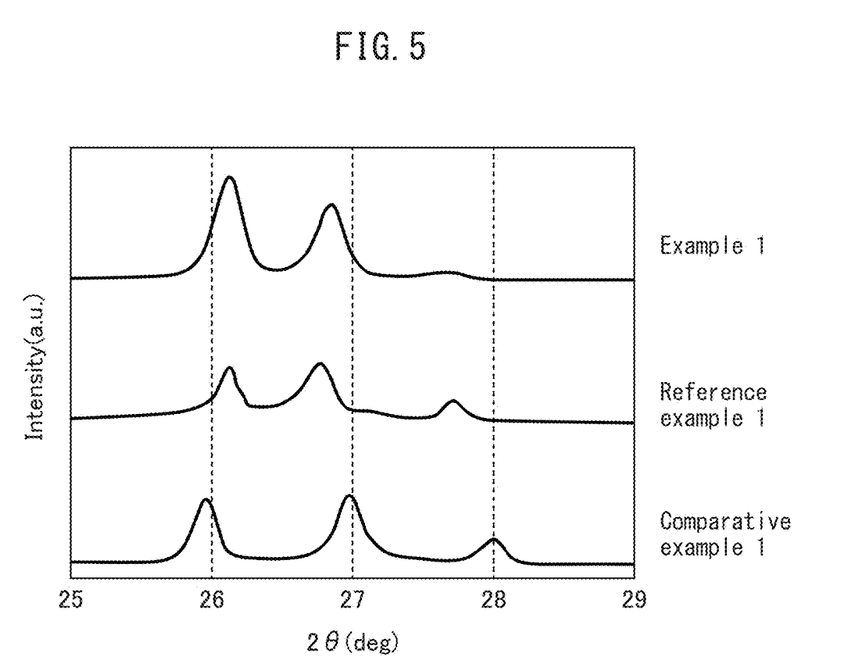
FIG. 5 is a chart showing the results of measuring the X-ray diffraction of particles obtained according to the methods of Example 1, Reference Example 1 and Comparative Example 1.

FIG. 5 indicates a comparison of the results of carrying out X-ray diffraction on crystals obtained according to the methods of Example 1, Reference Example 1 and Comparative Example 1, respectively.

As shown in FIG. 5, a first peak is present at $2\theta=25.94$, a second peak is present at $2\theta=26.96$ and a third peak is present at $2\theta=28.00$ in the case of Comparative Example 1. A first peak is present at $2\theta=26.14$, a second peak is present at $2\theta=26.80$ and a third peak is present at $2\theta=27.67$ in the case of Example 1. A first peak is present at $2\theta=26.12$, a second peak is present at $2\theta=26.76$ and a third peak is present at $2\theta=27.70$ in the case of Reference Example 1.

The first peaks present in Example 1 and Reference Example 1 are shifted to the right relative to that of Comparative Example 1, while the second and third peaks are each shifted to the left.

The peak at around 2θ=26 is assigned to LiI ((111) plane), the peak at around 2θ=27 is assigned to $Li_2S$ ((111) plane), and the peak at around 2θ=28 is assigned to LiBr ((111) plane).

As the shifts of these peaks become larger, the degree to which anions of other salts are in solid solution in the crystals indicated by these peaks can be said to become greater. For example, a shift towards a higher angle by the peak of LiI indicates that the crystal lattice of LiI has contracted, and this contraction of the crystal lattice is caused by bromide ions or sulfide ions, having a smaller diameter than iodide ions, having taken the place of and entered those locations occupied by iodide ions in the crystal.

On the basis of these results, the precipitates of Example 1 and Reference Example 1 are thought to consist of crystals that are in a complexed state to a greater degree than the precipitate of Comparative Example 1.

(Evaluation 3)

Figure 6:
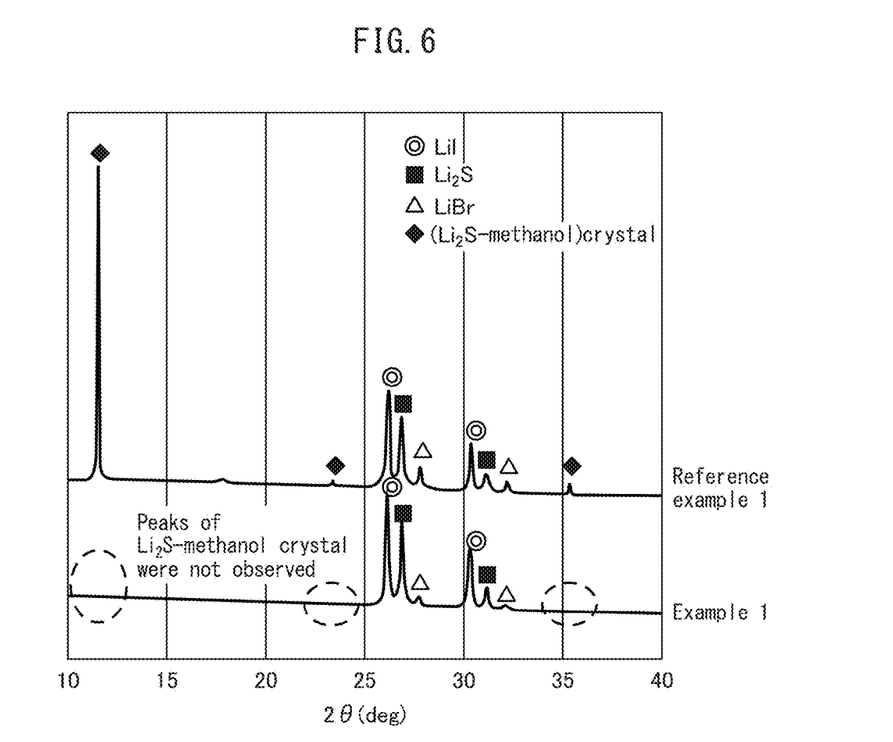
FIG. 6 is a chart showing the results of measuring the X-ray diffraction of particles obtained according to the methods of Example 1 and Reference Example 1.

FIG. 6 is a chart showing the results of measuring X-ray diffraction of precipitates obtained according to the methods of Example 1 and Reference Example 1, respectively. It can be determined from FIG. 6 that peaks at 2θ=11.64, 23.36 and 35.38 assigned to the $Li_2S$-methanol crystal observed in Reference Example 1 were not observed in particles obtained according to the method of Example 1. On the basis of this result, it can be concluded that precipitation of crystals resulting from the reaction between $Li_2S$ and methanol is inhibited by the method of Example 1.

(Evaluation 4)

Figure 7:
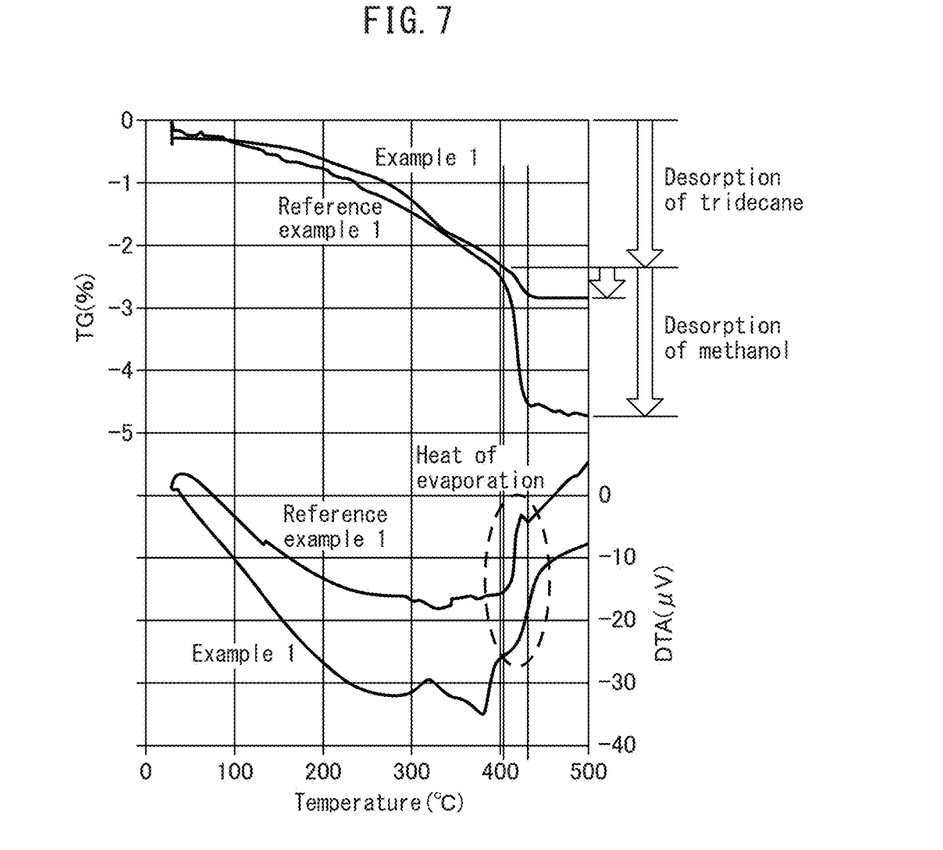
FIG. 7 is a chart showing the results of TG/DTA for particles obtained according to the methods of Example 1 and Reference Example 1.

FIG. 7 is a chart showing the results of TG/DTA carried out on particles obtained according to the methods of Example 1 and Reference Example 1, respectively. In FIG. 7, the amount of the change in weight at around 400° C. indicates the mass of methanol contained in the particles. In the case of the particles obtained in Example 1, the change in weight at this temperature range is about 0.5%, indicating that there is little methanol contained in the particles. Namely, according to the production method of Example 1, not only are a plurality of raw material components complexed and particles are obtained that have undergone low crystal growth, particles can be determined to be able to be obtained that have only a small amount of residual methanol present therein.

BRIEF DESCRIPTION OF THE REFERENCE SYMBOLS

10 Reaction vessel
20 Heating device
30 Good solvent solution
40 Single-fluid spraying nozzle
41 Spray nozzle
50 Droplets of good solvent solution
51 Atomized good solvent solution
60 Poor solvent
70 Flowing gas
80 Vessel
85 Reaction raw material vessel

The invention claimed is:

1. A method for producing complexed particles, wherein the method comprises:
    obtaining a good solvent solution, by dissolving $Li_2S$, and LiX (X is at least one selected from a group consisting of F, Cl, Br, and I) in a good solvent, and
    precipitating particles by contacting the good solvent solution with a poor solvent having a temperature at least 165° C. higher than the boiling point of the good solvent, to evaporate off the good solvent; and,
    wherein the method satisfies at least one of the following:
    (i) the good solvent solution being obtained by further dissolving $H_2S$ in the good solvent, and (ii) $H_2S$ being dissolved in the poor solvent.

2. The method according to claim 1, wherein the LiX is LiI and LiBr.

3. The method according to claim 1, wherein at least the (i) is satisfied.

4. The method according to claim 3, wherein in the (i), the good solvent solution is obtained by further dissolving $H_2S$ in the good solvent by blowing $H_2S$ into the good solvent.

5. The method according to claim 1, wherein at least the (ii) is satisfied.

6. The method according to claim 5, wherein in the (ii), the $H_2S$ is dissolved in the poor solvent by blowing $H_2S$ into the poor solvent.

7. The method according to claim 1, wherein the ratio of the LiX (X is at least one selected from a group consisting of F, Cl, Br, and I) is 0.30 mol to 0.60 mol based on 1 mol of $Li_2S$.

8. A method for producing complexed particles, wherein the method comprises:
    obtaining a good solvent solution, by dissolving LiHS, and LiX (X is at least one selected from a group consisting of F, Cl, Br, and I) in a good solvent, and
    precipitating particles by contacting the good solvent solution with a poor solvent having a temperature at least 165° C. higher than the boiling point of the good solvent to evaporate off the good solvent.

9. The method according to claim 8, wherein the ratio of the LiX (X is at least one selected from a group consisting of F, Cl, Br, and I) is 0.30 mol to 0.60 mol based on 1 mol of LiS.

10. The method according to claim 8, wherein the LiX is LiI and LiBr.

11. The method according to claim 1, wherein the contacting the good solvent solution with the poor solvent is by dropping, spraying, or injecting the good solvent solution into the poor solvent.

12. The method according to claim 11, wherein the contacting the good solvent solution with the poor solvent is by dropping the good solvent solution into the poor solvent.

* * * * *